US012612356B2

(12) United States Patent
Riebel et al.

(10) Patent No.: US 12,612,356 B2
(45) Date of Patent: Apr. 28, 2026

(54) PROCESS FOR NITRATE ESTER FORMATION OF AN α,ω-ALKANEDIOL MONOACYLATE

(71) Applicant: DSM IP ASSETS B.V., Heerlen (NL)

(72) Inventors: Peter Hans Riebel, Kaiseraugst (CH); Angela Wildermann, Kaiseraugst (CH)

(73) Assignee: DSM IP Assets B.V. (NL)

( * ) Notice: Subject to any disclaimer, the term of this patent is extended or adjusted under 35 U.S.C. 154(b) by 710 days.

(21) Appl. No.: 17/919,932

(22) PCT Filed: Apr. 21, 2021

(86) PCT No.: PCT/EP2021/060406
§ 371 (c)(1),
(2) Date: Oct. 19, 2022

(87) PCT Pub. No.: WO2021/214145
PCT Pub. Date: Oct. 28, 2021

(65) Prior Publication Data
US 2023/0150916 A1 May 18, 2023

(30) Foreign Application Priority Data

Apr. 22, 2020 (EP) .................................... 20170758

(51) Int. Cl.
*C07C 201/02* (2006.01)
*C07C 67/08* (2006.01)
*C07C 203/02* (2006.01)
(52) U.S. Cl.
CPC ............ *C07C 201/02* (2013.01); *C07C 67/08* (2013.01); *C07C 203/02* (2013.01)

(58) Field of Classification Search
CPC .................................................... C07C 201/02
See application file for complete search history.

(56) References Cited

U.S. PATENT DOCUMENTS

| | | | |
|---|---|---|---|
| 7,632,960 B2 | 12/2009 | Pöhlmann et al. | |
| 10,450,590 B2 | 10/2019 | Haas et al. | |
| 2010/0137599 A1 | 6/2010 | Hack et al. | |

FOREIGN PATENT DOCUMENTS

| | | | | |
|---|---|---|---|---|
| CN | 1978423 | 6/2007 | | |
| CN | 101730676 | 6/2010 | | |
| EP | 2048129 | * 4/2009 | .......... | C07C 201/02 |
| EP | 2759598 | 7/2014 | | |
| GB | 432488 | * 7/1935 | .......... | C07C 201/02 |
| WO | WO2009000723 | * 12/2008 | .......... | C07C 201/02 |
| WO | 2012/084629 | 6/2012 | | |
| WO | WO 2019/115503 | 6/2019 | | |

OTHER PUBLICATIONS

International Search Report for PCT/EP2021/060406, mailed Jun. 29, 2021, 3 pages.
Written Opinion of the ISA for PCT/EP2021/060406, mailed Jun. 29, 2021, 5 pages.
Second Examination Opinion Notice, CN Application No. 202180029958.1, Dec. 9, 2024.

* cited by examiner

*Primary Examiner* — Paul V Ward
(74) *Attorney, Agent, or Firm* — Jed C. Benson

(57) ABSTRACT

The invention relates to a safe and efficient process for the nitrate ester formation of an α,ω-$C_{3-10}$alkanediol monoacylate. The process is safer to operators and allows to obtain advantageous yields on industrial scale.

15 Claims, 2 Drawing Sheets

1

PROCESS FOR NITRATE ESTER FORMATION OF AN α,ω-ALKANEDIOL MONOACYLATE

This application is the U.S. national phase of International Application No. PCT/EP2021/060406 filed Apr. 21, 2021 which designated the U.S. and claims priority to EP patent application Ser. No. 20/170,758.5 filed Apr. 22, 2020, the entire contents of each of which are hereby incorporated by reference.

The invention relates to a safe and efficient process for the manufacture of ω-nitrooxy-$C_{3-10}$alkane-1-ols.

Global temperature is increasing, a process referred to as global warming or climate change. One of the main focuses to reduce this warming effect is to reduce the amount of greenhouse gases emitted into the atmosphere. Greenhouse gases are emitted from several different sources, both natural and anthropogenic; however, the two sources with the biggest impact are the agricultural and fossil fuel industries. Within agriculture, ruminants and in particular cattle are the major contributors to the biogenic methane formation, and it has been estimated that the prevention of methane formation from ruminants would almost stabilize atmospheric methane concentrations.

3-Nitrooxypropanol (3-NOP, also known as 3-nitrooxy-propan-1-ol or 1,3-propanediol mononitrate) has been reported to be highly efficient in reducing the formation of methane in ruminants without affecting microbial fermentation in a way that would be detrimental to the host animal (WO-2012/084629). Furthermore, WO-2012/084629 discloses the preparation of 3-nitrooxypropanol by reacting 3-bromopropanol in acetonitrile with silver nitrate, a process which is, however, not economical in industrial scale production.

A potential route for industrial scale production of ω-nitrooxy-$C_{3-10}$alkane-1-ols involves direct nitrate ester formation of the respective α,ω-alkanediols. This reaction, however, is often poorly selective and leads to the formation of significant amounts of dinitrated alkanediols. Furthermore, this route requires high safety measures since organic nitrates and even more dinitrates are explosive and therefore difficult to handle, even in diluted solution.

An alternative to the direct nitrate ester formation of α,ω-alkanediols is a three-step process encompassing the interim protection of one of the two alcohol groups prior to nitrate ester formation, e.g. by acetylation, followed by nitrate ester formation and consecutive removal of the respective protecting group after the nitrate ester formation step. However, even though the safety and the selectivity may thus be increased, the additional reaction steps normally lead to a significant loss in the overall yield and a substantial increase in processing cost.

Thus, there is an ongoing need for the optimization of the three-step process allowing safe and economical production of ω-nitrooxy-$C_{3-10}$alkane-1-ols in large quantities starting from α,ω-alkanediols. Furthermore, there is a need for workup strategies to allow a quantitative recovery of reactants as well as solvents.

Surprisingly it has now been found that ω-nitrooxy-$C_{3-10}$alkane-1-ols such as in particular 3-nitrooxypropanol can be obtained in high yields in a highly specialized three-step process, while at the same time maintaining the reaction stability and thus ensuring process safety.

Said process encompasses the consecutive steps of (a) acylation of the corresponding α,ω-alkanediol with an acylating agent, (b) nitrate ester formation of the resulting α,ω-$C_{3-10}$alkanediol monoacylate with a nitrating agent to form a α,ω-$C_{3-10}$alkanediol mononitrate monoacylate followed by (c) hydrolysis of the acyl group to obtain the respective α,ω-$C_{3-10}$alkanediol mononitrate and optionally (d) solvent work-up.

The individual steps (a) to (d) are novel.

Thus in a first embodiment, the present invention relates to (B) Continuous nitrate ester formation of the α,ω-$C_{3-10}$alkanediol monoacylate by reacting a nitrating agent with a solution comprising the α,ω-$C_{3-10}$alkanediol monoacylate and an inert solvent in a group of pieces of equipment comprising at least two reactors in series by simultaneously feeding said solution into the first and the second reactor to obtain the respective α,ω-$C_{3-10}$ alkanediol mononitrate monoacylate, In a further embodiment the present invention relates to a process for the preparation of an α,ω-$C_{3-10}$alkanediol mononitrate, preferably of propanediol mononitrate, said process comprising next to step (B) outlined above the following steps: (A) before and (C) and optionally (D) consecutively after said step (B), said steps being (A) Acylation of an α,ω-alkanediol with an acylation agent (acylation reaction), said acylation comprising the step of re-feeding recycled reaction components comprising α,ω-$C_{3-10}$alkanediol, α,ω-$C_{3-10}$alkanediol monoacylate and α,ω-$C_{3-10}$alkanediol diacylate back into said acylation reaction, with the proviso that in the acylation reaction per mole recycled acylate groups 0.5 to 1.5 mole of water is present and that the molar ratio of the (molar) sum of the acylating agent, α,ω-$C_{3-10}$alkanediol monoacylate and 2 times of α,ω-$C_{3-10}$alkanediol diacylate to the sum of the α,ω-$C_{3-10}$alkanediol, α,ω-$C_{3-10}$alkanediol monoacylate and α,ω-$C_{3-10}$alkanediol diacylate is selected in the range 0.5 to 1.1 mol per mol of α,ω-$C_{3-10}$alkanediol, preferably in the range from 0.6 to 1 mol, most preferably in the range from 0.75 to 1 mol, (C) Two-phase hydrolysis of the α,ω-$C_{3-10}$alkanediol mononitrate monoacylate by continuously feeding a base and a solution comprising the α,ω-$C_{3-10}$alkanediol mononitrate monoacylate and an inert solvent into a stirred cascade reactor to obtain a solution comprising the inert solvent and α,ω-$C_{3-10}$ alkanediol mononitrate, and optionally (D) Removal and recovery of the inert solvent from the solution by distillation, said distillation comprising partial condensation and continuous back-feeding of liquid fractions comprising mixtures of inert solvent and α,ω-$C_{3-10}$ alkanediol mononitrate into said distillation.

Definition of Terms

The term 'α,ω-$C_{3-10}$alkanediols' as used herein refers to linear α,ω-alkanediols having 3 to 10 carbon atoms such as 1,3-propanediol, 1,4-butanediol, 1,5-pentanediol, 1,6-hexanediol, 1,7-heptanediol, 1,8-octanediol, 1,9-nonanediol and 1,10-decanediol. The most preferred α,ω-$C_{3-10}$alkanediol in all embodiments according to the present invention is 1,3-propanediol (also referred to herein as PD).

The term 'α,ω-$C_{3-10}$alkanediol monoacylate' as used herein refers to the linear α,ω-alkanediols as defined above, wherein one of the hydroxyl groups has been esterified. Preferably, the acyl moiety is a linear or branched $C_{1-6}$ acyl group, more preferably a linear or branched $C_{1-4}$ acyl group such as most preferably acetyl (—C(=O)—CH$_3$). Particularly preferred in all embodiments according to the present invention are the 1,3-propanediol monoacylates. The most preferred α,ω-$C_{3-10}$alkanediol monoacylate in all embodiments of the present invention is 1,3-propanediol monoacetate (also referred to herein as PDMA).

The term 'α,ω-$C_{3-10}$alkanediol diacylate' as used herein refers to the linear α,ω-alkanediols as defined above, wherein both of the hydroxyl groups have been esterified. Particularly preferred in all embodiments according to the present invention are the 1,3-propanediol diacylates. The most preferred α,ω-$C_{3-10}$alkanediol diacylate in all embodiments of the present invention is 1,3-propanediol diacetate (also referred to herein as PDDA).

The term 'α,ω-$C_{3-10}$alkanediol mononitrate' as used herein refers to the linear α,ω-alkanediols as defined above wherein one of the hydroxyl groups has been nitrated such 3-nitrooxypropane-1-ol (also referred to as 3-nitrooxypropanol or 3-hydroxypropyl-1-nitrate), 4-nitrooxybutane-1-ol, 5-nitrooxypentane-1-ol, 6-nitrooxyhexane-1-ol, 7-nitrooxyheptane-1-ol, 8-nitrooxyoctane-1-ol, 9-nitrooxynonane-1-ol and 10-nitrooxydecane-1-ol. Particularly preferred in all embodiments according to the present invention is 3-nitrooxypropane-1-ol (also referred to herein as propanediol mononitrate or PDMN).

The term 'α,ω-$C_{3-10}$alkanediol mononitrate monoacylate' as used herein refers to the α,ω-$C_{3-10}$alkanediol monoacylates as defined above wherein the remaining hydroxyl group has been nitrated. Particularly preferred in all embodiments according to the present invention are the 1,3-propanediol mononitrate monoacylates. The most preferred α,ω-$C_{3-10}$alkanediol mononitrate monoacylate in all embodiments according to the present invention is 1,3-propanediol mononitrate monoacetate (also referred herein to as PDMNMA).

The term 'α,ω-alkanedioldinitrates' as used herein refers to the linear α,ω-alkanediols as defined above wherein both hydroxyl groups have been nitrated, such as 1,3-propanediol dinitrate, 1,4-butanediol dinitrate, 1,5-pentanediol dinitrate, 1,6-hexanediol dinitrate, 1,7-heptanediol dinitrate, 1,8-octanediol dinitrate, 1,9-nonanediol dinitrate and 1,10-decanediol dinitrate. Particularly preferred in all embodiments according to the present invention is 1,3-propanediol dinitrate (also referred herein to as PDDN).

The term 'inert solvent' (also abbreviated as 'S') as used herein is understood as meaning a solvent which does not take part in a chemical reaction in the reaction medium and under the operating conditions, and which is inert to both the reactants and the reaction products. In a preferred embodiment, the inert solvent is a halogenated solvent. The term 'halogenated solvent' means a solvent containing one or more halogen atoms and refers to any solvent selected from, but is not limited to, dichloromethane, diiodomethane, carbon tetrachloride, dichloroethane, or chloroform. Most preferably in all embodiments of the present invention, the inert solvent is dichloromethane (also referred to herein as DCM).

The term 'consisting essentially of' as used according to the present invention means that besides the listed components/ingredients/solvents etc. no further components are purposively added. It is however not excluded that small amount of impurities introduced by the respective raw materials may be present.

Nitrate Ester Formation

The invention relates to a continuous nitrate ester formation process for the preparation of α,ω-$C_{3-10}$alkanediol mononitrate monoacylates, said process comprising reacting a nitrating agent with a solution comprising the respective α,ω-$C_{3-10}$alkanediol monoacylate and an inert solvent (in the following also referred to as (B-I)) in a group of pieces of equipment comprising at least two reactors in series, characterized in that the solution is simultaneously fed into the first (also referred to as reactor B1) and the second (also referred to as reactor B2) reactor (see FIG. 2).

Preferably, the nitrate ester formation is carried out continuously in a flow-reactor as e.g. depicted in FIG. 2.

A flow reactor according to this invention is a device in which chemical reactions take place in channels or tubes. The flow reactor is generally operated continuously (in contrast with/to a batch reactor) and has channels/tubes in which the reaction takes place (such as the reactors B1 and B2 in FIG. 2). The reaction stoichiometry is defined by the concentration of reagents and the ratio of their flow rate. The (mean) residence time is given by the ratio of volume of the reactor and the overall flow rate. The flow reactor preferably comprises (static) mixing elements, such as SMX mixer or Kenics mixer.

The term "residence time" as used herein refers to the volume of the reaction zone divided by the outlet volumetric flow rate of reactants at the reaction system's temperature and pressure. In a specific embodiment of the invention the mean residence time is calculated with the density of the respective outlet temperature of the reactor.

Preferably, the mass flow ratio of the solution (B-I) into the first reactor is selected in the range of 40 to 60% of the total mass flow of the solution (B-I), the remaining is fed to the second reactor.

The term "mass flow" or "mass flow rate" as used herein may include not only the actual or measured mass flow rate, but also the calculated mass flow rate. It generally refers to the mass flow rate of a reaction solution as measured in the corresponding feed lines. This mass flow rate can be calculated or measured with a suitable sensor located in the corresponding feed lines.

In a particular advantageous embodiment the continuous nitrate ester formation according to the present invention comprises the following consecutive steps:

(N-1) Provision of a continuously operated flow-reactor comprising at least two reactors, reactor (1) (also referred to herein as B1) and reactor (2) (also referred to herein as B2), in series (N-2) Provision of a solution comprising an α,ω-$C_{3-10}$alkanediol monoacylate and an inert solvent (i.e. B-I), and (N-3) Feeding of reactor (1) with a nitrating agent and a first portion of said solution, followed by (N-4) Adding a second portion of said solution into the reactor (2), with the proviso that the mass flow of the solution into the reactor 1 is selected in the range of 40 to 60% of the total mass flow of the solution, while the remaining solution is fed into reactor 2.

The term "nitrating agent" (also referred to herein as NA) as used herein refers to a compound which when reacted with a reactant substrate forms a compound with a nitrate ester (—O—$NO_2$) group. Exemplary nitrating agents include, but are not limited to, nitric acid and nitrate salts, such as alkali metal nitrate salts, e.g., $KNO_3$, as well as nitrosulfuric acid (i.e. a mixture of nitric acid and sulphuric acid)

In all embodiments of the present invention, the nitrating agent is preferably nitric acid applied as nitrosulfuric acid, i.e. a mixture of nitric acid and sulphuric acid.

In the continuous nitrate ester formation according to the present invention, preferably 1.5 to 2.5 mol equivalents, more preferably 1.7 to 2.3 mol equivalents, most preferably 1.9 to 2.0 mol equivalents of $H_2SO_4$, based on $HNO_3$ is used.

In the continuous nitrate ester formation according to the present invention, preferably from 1 to 1.5 mol equivalents, more preferably from 1.1 to 1.2 mol equivalents of $HNO_3$, based on the $\alpha,\omega$-$C_{3-10}$alkanediol monoacylate is used.

In the continuous nitrate ester formation according to the present invention it is furthermore preferred that the reaction volume of the reactor (1) to the reactor (2) is selected in the range from 4:1 to 1:4, preferably from 3:1 to 1:3, most preferably from 2:1 to 1:2.

The continuous nitrate ester formation is preferably carried out for a mean residence time in both reactors (i.e. in reactor (1) and reactor (2) (FIG. 2: in B1 and B2) ranging from about 5 to about 30 seconds, preferably from about 10 to about 20 seconds, most preferably from about 15 to 19 seconds.

Preferably in all embodiments of the continuous nitrate ester formation, the solution (i.e. B-I) consists essentially of the $\alpha,\omega$-$C_{3-10}$alkanediol monoacylate and the inert solvent.

The term 'consisting essentially of' as used according to the present invention means that besides the listed components/ingredients/solvents no further components are purposively added. It is however not excluded that small amount of impurities introduced by the respective raw materials may be present.

Even more preferably, the concentration of the $\alpha,\omega$-$C_{3-10}$alkanediol monoacylate in the inert solvent is selected in the range from 10 and 60 wt.-%, more preferably from 20 and 50 wt.-% and most preferably from 35 and 45 wt.-%, the remainder being the inert solvent.

In a particular advantageous embodiment the continuous nitrate ester formation according to the present invention further comprises the following steps:

(N-5a) Quenching (in B3) the reaction mixture (also referred to herein as NRM) with water, optionally in the presence of a base resulting in a biphasic mixture (also referred to herein as NBM) consisting of an organic and aqueous phase, (N-5b) Phase separation (in B4) of the biphasic mixture (NBM) to obtain an organic (also referred to herein as NOP) and an aqueous phase (also referred to herein as NAP), (N-5c) optionally Concentrating the aqueous phase (NAP) from phase separation to recover $H_2SO_4$ if no base was used for neutralization, and (N-5d) optionally Washing the organic phase (NOP) obtained in (N-5c) at least once with water and/or drying the organic phase.

A particularly preferred continuous nitrate ester formation is outlined in FIG. 2, which continuous nitrate ester formation consists of the consecutive steps (N-1), (N-2), (N-3), (N-4), (N-5a), (N-5b) and (N-5c).

It is well understood that the continuous nitrate ester formation according to the present invention may also comprise the step of isolating/concentrating the $\alpha,\omega$-$C_{3-10}$alkanediol mononitrate monoacylate from the organic phase (NOP) e.g. by (partial) distillation of the solvent.

The nitrate ester formation reaction mixture (NRM) in all embodiments of the present invention preferably consists essentially of the remaining/unreacted nitrating agent, $\alpha,\omega$-$C_{3-10}$alkanediol mononitrate monoacylate, unreacted $\alpha,\omega$-$C_{3-10}$alkanediol monoacylate and inert solvent.

Suitable bases include alkali or earth alkali bases such as alkali or earth alkali hydroxides or carbonates as well as ammonia, amines without being limited thereto. The base is preferably selected from the group of NaOH (caustic), KOH, $Ca(OH)_2$ or ammonia, more preferably an aqueous solution thereof is used. Most preferably in all embodiments of the present invention the base is aqueous NaOH (caustic).

In the continuous nitrate ester formation according to the present invention preferably no base is used for quenching.

Thus, in a further particular advantageous embodiment, the quenching of the nitrate ester formation reaction mixture (NRM) is performed either with cold water, such as with water having a temperature selected in the range from 0 to 20° C., more preferably in the range from 5 to 15° C.

In the continuous nitrate ester formation according to the present invention, advantageously, the outlet reaction temperature of the reactor (1) is equal to or below 40° C., preferably 30° C., more preferably 20° C., more preferably 10° C. and most preferably equal to or below 5° C. The outlet reaction temperature of reactor (2) can be slightly higher. Preferably, however the outlet temperature of reactor (2) is selected in the range of 15 to 25° C.

Advantageously, in all embodiments, the reaction temperature for the quenching step (N-6a) is equal to or below 20° C., preferably equal to or below 15° C., more preferably equal to or below 10° C.

Acylation

In a preferred embodiment, the process according to the present invention also comprises a step (A) which precedes step (B), which step (A) is directed to the acylation of an $\alpha,\omega$-alkanediol with an acylation agent (acylation reaction), said acylation comprising the step of re-feeding recycled reaction components into said acylation reaction as outlined above.

It is well understood, that the acylation may further comprise the steps of isolation and/or purification of the obtained $\alpha,\omega$-$C_{3-10}$alkanediol monoacylate by the methods disclosed herein or any other suitable method in the art.

It is well understood, that the term 'reaction components' as used herein refers to components of the acylation reaction which take part in the acylation reaction, i.e. the $\alpha,\omega$-alkanediol, the $\alpha,\omega$-$C_{3-10}$alkanediol monoacylate and the $\alpha,\omega$-$C_{3-10}$alkanediol diacylate as well as the acylating agent and water, not encompassing, however, any solvents or other inert ingredients or additives.

In all embodiments of the present invention, the term 'recycled reaction components' (also abbreviated as RRC) refers to unreacted $\alpha,\omega$-$C_{3-10}$alkanediol, $\alpha,\omega$-$C_{3-10}$alkanediol monoacylate and $\alpha,\omega$-$C_{3-10}$alkanediol diacylate as well as water and acylating agent.

It is furthermore well understood, that the recycled reaction components can be isolated separately or as any mixture thereof and thus be re-fed individually or as any mixture thereof. Preferably, the recycled reaction components consist essentially of (1) a mixture of $\alpha,\omega$-$C_{3-10}$alkanediol monoacylate and $\alpha,\omega$-$C_{3-10}$alkanediol diacylate (RCC-(I))

(2) unreacted $\alpha,\omega$-$C_{3-10}$alkanediol (RCC-(II)) as well as (3) a mixture of water and acylating agent (RCC-(III)).

In all embodiments of the present invention it is preferred that at least the recycled reaction components RCC-(I) and RCC-(II) are admixed before being re-fed into the acylation reaction (see FIG. 1).

The acylation according to the present invention can be carried out batch wise or continuously.

Preferably, the acylation of the $\alpha,\omega$-alkanediols with an acylation agent according to the present invention is carried out in a reactor into which the recycled reaction components are (continuously) re-fed.

Suitable reactors include any type of vessel, such as stirred tank reactors, cascade reactors, loop reactors, tubular reactors, without being limited thereto.

In a particular embodiment, the acylation according to the present invention further comprises the step of separation of the obtained $\alpha,\omega$-$C_{3\text{-}10}$alkanediol monoacylate by distillation, preferably in a way such that the amount of $\alpha,\omega$-$C_{3\text{-}10}$alkanediol in the $\alpha,\omega$-$C_{3\text{-}10}$alkanediol monoacylate is less than 0.5 wt.-%, preferably less than 0.1 wt.-%, based on the $\alpha,\omega$-$C_{3\text{-}10}$alkanediol monoacylate and the amount of the $\alpha,\omega$-$C_{3\text{-}10}$alkanediol diacylate in the $\alpha,\omega$-$C_{3\text{-}10}$alkanediol monoacylate is less than 5 wt. %, preferably less than 2.5 wt.-%, based on the $\alpha,\omega$-$C_{3\text{-}10}$alkanediol monoacylate.

It is furthermore preferred that during said separation the reaction components to be recycled are collected.

Preferably, in all embodiments of the present invention, the acylation and the consecutive separation of the $\alpha,\omega$-$C_{3\text{-}10}$alkanediol monoacylate is a (fully) continuous process carried out in a vessel cascade set-up or a cascade reactor as e.g. outlined in FIG. 1).

A vessel cascade set-up (also called reactor cascade set-up) for the purpose of the invention is a setup that comprises at least two consecutive vessels, in which the reaction can be performed and wherein each step can only be performed after the previous one. The vessels/reactors can be of the same or different types. It is well understood by a person skilled in the art that the vessel cascade set-up may include devices for separation and/or distillation.

A cascade reactor for the purpose of the invention is a setup that comprises an outer reactor shell with at least one inlet at one end and at least one outlet at the opposite end, optional additional outlets for vapor and/or by-product removal, and optional ports for monitoring, sampling and/or mixing. Within the reactor, a series of two or more segmented reaction chambers (corresponding to at least two consecutive vessels) may be defined by partitions, in which the reaction can be performed and wherein each chamber/partition can only be flown through after the previous one. The reactor is preferably suitable for multiple different chemical reactions and need not be custom-made for a particular reaction. The cascade reactor may, for example be a flow reactor.

In a particular embodiment of the present invention, the acylation (including the subsequent separation of the obtained $\alpha,\omega$-$C_{3\text{-}10}$alkanediol monoacylate) is a process encompassing the steps of (A-1) Acylation of an $\alpha,\omega$-$C_{3\text{-}10}$alkanediol with an acylating agent (acylation reaction) in an initial vessel, with the proviso that in said acylation reaction per mole recycled acylate groups 0.5 to 1.5 mole of water is present and the molar ratio of the (molar) sum of the acylating agent, $\alpha,\omega$-$C_{3\text{-}10}$alkanediol monoacylate and 2 times of $\alpha,\omega$-$C_{3\text{-}10}$alkanediol diacylate to the sum of the $\alpha,\omega$-$C_{3\text{-}10}$alkanediol, $\alpha,\omega$-$C_{3\text{-}10}$alkanediol monoacylate and $\alpha,\omega$-$C_{3\text{-}10}$alkanediol diacylate is selected in the range from 0.5 to 1.1 mol per mol of $\alpha,\omega$-$C_{3\text{-}10}$alkanediol (also referred to as acetylation reaction mixture or ARM), (A-2) Removal of the acylating agent and water to form a mixture comprising unreacted $\alpha,\omega$-$C_{3\text{-}10}$alkanediol as well as mono- and diacylated $\alpha,\omega$-$C_{3\text{-}10}$alkanediol (also referred to as AM-I), (A-3) Separation of the $\alpha,\omega$-$C_{3\text{-}10}$alkanediol monoacylate from said mixture (i.e. from AM-I) by distillation such that the thus obtained $\alpha,\omega$-$C_{3\text{-}10}$alkanediol monoacylate contains less than 0.5 wt.-% of $\alpha,\omega$-$C_{3\text{-}10}$alkanediol and less than 5 wt.-% of $\alpha,\omega$-$C_{3\text{-}10}$alkanediol diacylate, (A-4) Collecting the reaction components to be recycled, and (A-5) Re-feeding the recycled reaction components comprising at least $\alpha,\omega$-$C_{3\text{-}10}$alkanediol, $\alpha,\omega$-$C_{3\text{-}10}$alkanediol monoacylate and $\alpha,\omega$-$C_{3\text{-}10}$alkanediol diacylate into the initial vessel.

In all embodiments of the present invention it is preferred that within the acylation reaction, such as in particular in step (A-1) per mole recycled acylate groups preferably 0.75 to 1.25 mole, most preferably 0.85 to 1.1 mole such as in particular 0.95 to 1.05 mole of water is present, and the molar ratio of the (molar) sum of the acylating agent, $\alpha,\omega$-$C_{3\text{-}10}$alkanediol monoacylate and 2 times $\alpha,\omega$-$C_{3\text{-}10}$alkanediol diacylate to the sum of the $\alpha,\omega$-$C_{3\text{-}10}$alkanediol, $\alpha,\omega$-$C_{3\text{-}10}$alkanediol monoacylate and $\alpha,\omega$-$C_{3\text{-}10}$alkanediol diacylate is preferably selected in the range from 0.6 to 1 mol, most preferably in the range from 0.7 to 1 mol, such as in particular in the range from 0.75 to 1 mol.

The term 'per mole acylate groups' as used herein refers to the sum of acylate groups from the $\alpha,\omega$-$C_{3\text{-}10}$alkanediol monoacylate and the $\alpha,\omega$-$C_{3\text{-}10}$alkanediol diacylate (i.e. 1 mol for each $\alpha,\omega$-$C_{3\text{-}10}$alkanediol monoacylate and two moles for each $\alpha,\omega$-$C_{3\text{-}10}$alkanediol diacylate).

As already outlined above, the reaction components to be recycled in step (A-5) consist essentially of $\alpha,\omega$-$C_{3\text{-}10}$alkanediol, $\alpha,\omega$-$C_{3\text{-}10}$alkanediol monoacylate and $\alpha,\omega$-$C_{3\text{-}10}$alkanediol diacylate. However, it is not excluded by the present invention that the acylating agent and/or the water removed in step (A-2) can also be recycled and re-fed as deemed appropriate.

It is furthermore well understood, that, to adjust the ratios and amounts as defined herein, fresh $\alpha,\omega$-$C_{3\text{-}10}$alkanediol, water and/or acylating agent are added as needed.

Suitable acylating agents (also referred to herein to as AA) for the acylation processes according to the present invention are carboxylic acids and derivatives thereof such as e.g. the respective, esters and acyl halides thereof. Preferably, the acylating agent is selected from the group consisting of linear or branched $C_{1\text{-}6}$alkanoic acids respectively, esters or acid chlorides thereof, more preferably from linear $C_{1\text{-}4}$ carboxylic acids such as for example acetic acid, propanoic acid, butanoic acid and pentanoic acid. The most preferred acylating agent is acetic acid. Any acetic acid, i.e. also aqueous solutions thereof can be used in all embodiments of the acylation. It is however understood, that the water content has to be adjusted accordingly to comply with the requirements according to the present invention.

The reaction temperature for the acylation reaction is preferably selected in the range from 80 to 200° C., more preferably in the range from 100 to 160° C., most preferably in the range of 120 to 150° C. It is well understood, that the pressure has eventually to be adjusted according to the desired reaction temperature.

The reaction time for the acylation reaction (such as in particular in step (A-1)) is preferably selected in the range from 1 to 10 hours, preferably in the range from 2 to 8 hours, most preferably in the range from 3 to 6 hours.

The removal of the acylation agent and reaction water in step (A-2) is preferably performed by distillation at reduced pressure and heating, which can be easily adjusted by a person skilled in the art. Suitable pressures include 40 to 120 mbar abs.

The separation of the $\alpha,\omega$-$C_{3\text{-}10}$alkanediol monoacylate from the reaction mixture (i.e. from AM-I) is preferably performed such, that the amount of $\alpha,\omega$-$C_{3\text{-}10}$alkanediol diacylate therein is less than 4 wt.-%, more preferably less than 3 wt.-%, most preferably less than 2.5 wt.-% such as less than 1 wt.-%, and the amount of the respective $\alpha,\omega$-$C_{3\text{-}10}$alkanediol therein is less than 0.4 wt.-%, more preferably, less than 0.25 wt.-%, most preferably less than 0.2 wt.-%, such as in particular less than 0.1 wt.-% (all amounts based on the amount of the $\alpha,\omega$-$C_{3-10}$alkanediol monoacylate).

The amount of residual $\alpha,\omega$-$C_{3-10}$alkanediol diacylate and $\alpha,\omega$-$C_{3-10}$alkanediol in the isolated (distilled) $\alpha,\omega$-$C_{3-10}$alkanediol monoacylate is generally determined by GC chromatography using a FID detector.

In a particularly advantageous embodiment, the separation/purification of the $\alpha,\omega$-$C_{3-10}$alkanediol monoacylate (i.e. Step (A-3)) is performed in two consecutive steps, i.e.

Step (A-3') consisting of distilling off the majority of the $\alpha,\omega$-$C_{3-10}$alkanediol diacylate from the mixture (AM-I) obtained in step (A-2) until a mixture (AM-Ia) is obtained, which consists essentially of $\alpha,\omega$-$C_{3-10}$alkanediol and $\alpha,\omega$-$C_{3-10}$alkanediol monoacetate followed by Step (A-3") consisting of distilling off the $\alpha,\omega$-$C_{3-10}$alkanediol monoacylate from the mixture (AM-Ia) such that the amount of $\alpha,\omega$-$C_{3-10}$alkanediol in the distilled $\alpha,\omega$-$C_{3-10}$alkanediol monoacetate is as defined herein, while preferably recovering unreacted $\alpha,\omega$-$C_{3-10}$alkanediol.

The term consisting essentially in Step (A-3') does not exclude the presence of small amounts of $\alpha,\omega$-$C_{3-10}$alkanediol diacetate, which amounts however have to be controlled such, that the final amount of $\alpha,\omega$-$C_{3-10}$alkanediol diacetate in the $\alpha,\omega$-$C_{3-10}$alkanediol monoacetate is as defined herein. Preferably, said amount does however not exceed 3 mole.-%.

It is even more preferred, that step (A-3') and step (A-3") are performed in two distinct vessels (distillation set-ups).

In an even more preferred embodiment step (A-3') and step (A-3") are performed using two separate distillation columns.

In a particular embodiment, the mixture (AM-I) consists essentially of 40 to 60 mol-% of $\alpha,\omega$-$C_{3-10}$alkanediol, 30 to 50 mol-% of $\alpha,\omega$-$C_{3-10}$alkanediol monoacylate and 5-15 mol-% $\alpha,\omega$-$C_{3-10}$alkanediol diacylate.

In another particular embodiment, the mixture (AM-Ia) consists essentially of 50 to 70 mol-% of $\alpha,\omega$-$C_{3-10}$alkanediol and 30 to 50 mol-% of $\alpha,\omega$-$C_{3-10}$alkanediol monoacylate and up to 3 mol.-% of $\alpha,\omega$-$C_{3-10}$alkanediol diacylate.

The reaction components to be recycled, i.e. which are re-fed into the acylation reaction such as in particular into step (A-1) above generally consist of the distillate of step (A-3') consisting essentially of $\alpha,\omega$-$C_{3-10}$alkanediol monoacylate and $\alpha,\omega$-$C_{3-10}$alkanediol diacylate and the sump of step (A-3") consisting essentially of unreacted $\alpha,\omega$-$C_{3-10}$alkanediol.

Preferably, the distillate of step (A-3') consists essentially of 10 to 40 wt.-% of $\alpha,\omega$-$C_{3-10}$alkanediol monoacylate and 60 to 90 wt.-% of $\alpha,\omega$-$C_{3-10}$alkanediol diacylate and up to 5 wt.-% $\alpha,\omega$-$C_{3-10}$alkanediol.

Preferably the sump of step (A-3") consists essentially of more than 95 wt.-% of $\alpha,\omega$-$C_{3-10}$alkanediol, more preferably of more than 97 wt. %, most preferably of more than 99 wt.-%.

The $\alpha,\omega$-$C_{3-10}$alkanediol monoacylate obtained in step (A-3") preferably exhibits a purity of more than 95 wt.-%, preferably of more than 97 wt.-%, most preferably of more than 98.5 wt.-% as determined by GC analysis using a FID detector.

In a particular advantageous embodiment of the present invention, the acylation (including the subsequent separation of the obtained $\alpha,\omega$-$C_{3-10}$alkanediol monoacylate) is a process as outlined in FIG. 1 encompassing the steps of (A-0) Provision of a vessel cascade setup, (A-1') Acylation of the $\alpha,\omega$-$C_{3-10}$alkanediol with an acylating agent with all the definitions and preferences as given herein by loading the first vessel (V1) with the $\alpha,\omega$-$C_{3-10}$alkanediol, the acylating agent and the recycled reaction components to form a reaction mixture (ARM), followed by (A-2') Feeding the reaction mixture (ARM) onto a first distillation column (V2) and distilling off the acylating agent and water to form a mixture (AM-1) consisting essentially of unreacted $\alpha,\omega$-$C_{3-10}$alkanediol and mono- and diacylated $\alpha,\omega$-$C_{3-10}$alkanediol, followed by (A-3') Feeding the mixture (AM-1) onto a second distillation column (V3) and distilling off a mixture of $\alpha,\omega$-$C_{3-10}$alkanediol mono and diacylate (i.e. RRC-(I)) to form a mixture (AM-Ia) consisting essentially of $\alpha,\omega$-$C_{3-10}$alkanediol and $\alpha,\omega$-$C_{3-10}$alkanediol monoacetate, (A-3") Feeding the mixture (AM-Ia) onto a third distillation column (V4) and distilling off the $\alpha,\omega$-$C_{3-10}$alkanediol monoacylate such that the amount of $\alpha,\omega$-$C_{3-10}$alkanediol in the distilled $\alpha,\omega$-$C_{3-10}$alkanediol monoacetate is less than 0.1 wt.-% and while recovering the $\alpha,\omega$-$C_{3-10}$alkanediol from the sump (i.e. RCC-(II)), (A-4') Collecting and optionally mixing the reaction components to be recycled, and (A-5') Re-feeding the optionally admixed recycled reaction components RRC-(I) and RRC-(II) from step (iv) and (v) into the first reaction vessel (V1), with the proviso that in the first reactor vessel (a) per mole recycled acylate groups 0.5 to 1.5 mole, preferably 0.75 to 1.25 mole, most preferably 0.85 to 1.1 mole, such as in particular 0.95 to 1.05 mole of water is present, and (b) the molar ratio of the (molar) sum of the acylating agent, $\alpha,\omega$-$C_{3-10}$alkanediol monoacylate and 2 times of $\alpha,\omega$-$C_{3-10}$alkanediol diacylate to the sum of the $\alpha,\omega$-$C_{3-10}$alkanediol, $\alpha,\omega$-$C_{3-10}$alkanediol monoacylate and the $\alpha,\omega$-$C_{3-10}$alkanediol diacylate is adjusted in the range 0.5 to 1.1 mol per mol of $\alpha,\omega$-$C_{3-10}$alkanediol, preferably in the range from 0.6 to 1 mol, most preferably in the range of 0.7 to 1 mol such as in the range from 0.75 to 1 mol.

It is well understood, that the recycled reaction components (I) may contain $\alpha,\omega$-$C_{3-10}$alkanediol monoacylate such as in amounts of up to 45 wt.-% as determined by e.g. GC-analysis using FID detector.

Preferably, in all embodiments the recycled reaction components (II) consists of more than 90 wt.-% of $\alpha,\omega$-$C_{3-10}$alkanediol, more preferably of more than 95 wt. %, most preferably of more than 98 wt.-% of $\alpha,\omega$-$C_{3-10}$alkanediol, as determined by e.g. GC-analysis using a FID detector.

It is, of course, well understood, that all the definitions and preferences for the acylation (including the acylation reaction and separation) herein also apply to the processes comprising the steps (A-1) to (A-5) as well as (A-0) to (A-5').

Hydrolysis

In a preferred embodiment, the process according to the present invention also comprises a step (C) (following step (B)) directed to a process for a two-phase hydrolysis of an $\alpha,\omega$-$C_{3-10}$alkanediol mononitrate monoacylate (to the respective $\alpha,\omega$-$C_{3-10}$alkanediol mononitrate), preferably of 1,3-propanediol mononitrate monoacetate to 1,3-propanediol mononitrate, said process comprising continuously feeding a base and a solution comprising an $\alpha,\omega$-$C_{3-10}$alkanediol mononitrate monoacylate and an inert solvent such as in particular dichloromethane (DCM) into a stirred cascade reactor.

In the following, the solution comprising an $\alpha,\omega$-$C_{3\text{-}10}$alkanediol mononitrate monoacylate and an inert solvent is also referred to as HS-I (e.g. in FIG. 3).

The hydrolysis processes according to the present invention can be carried out batch wise or continuously. Preferably, the hydrolysis process is a (fully) continuous process.

In a particular advantageous embodiment, said hydrolysis process comprises the following consecutive steps:

(H-1) Provision of a vertical, stirred cascade reactor setup, (H-2) Continuous feeding of a solution comprising an $\alpha,\omega$-$C_{3\text{-}10}$alkanediol mononitrate monoacylate and an inert solvent together with a base to the first (bottom) chamber (hydrolysis reactor C1 in FIG. 3), (H-3) Transferring the hydrolysis reaction mixture (also referred to herein as HRM) comprising $\alpha,\omega$-$C_{3\text{-}10}$alkanediol mononitrate, the inert solvent and the remaining base solution into a decanter or vessel (FIG. 3: C2) for phase separation to obtain an organic solution (I) comprising the $\alpha,\omega$-$C_{3\text{-}10}$alkanediol mononitrate and the inert solvent (also referred to herein as HS-II) and an aqueous solution (also referred to herein as HS-III), followed by (H-4) Collecting the organic solution (I) comprising the $\alpha,\omega$-$C_{3\text{-}10}$alkanediol mononitrate and the inert solvent (i.e. HS-II), optionally followed by (H-5) Evaporating the inert solvent from the organic solution (I) by distillation.

An exemplary (while preferred) hydrolysis according to the present invention is illustrated in FIG. 3.

In a preferred embodiment, the hydrolysis process according to the present invention further contains an additional step (H-6), comprising the steps (H-6a) extracting the aqueous phase (HS-II) obtained in step (H-3) with an additional amount of the inert solvent to recover further $\alpha,\omega$-$C_{3\text{-}10}$alkanediol mononitrate to yield an additional organic phase (II) (also referred to herein as HS-IV), and (H-6b) Co-feeding said organic phase (II) into step (H-5).

The hydrolysis process is preferably carried out in (continuously) in a vessel cascade set-up or a cascade reactor, more preferably in a vertical, stirred cascade reactor. In a preferred embodiment of the invention, the hydrolysis process is performed in a vertical, stirred cascade reactor with at least 10 chambers.

For the purpose of hydrolysis process a vertical, stirred cascade reactor is a vertical reactor, that is also a stirred reactor. The term "vertical reactor" or "horizontal reactor vessel", as used herein, means a reactor vessel having a longitudinal axis which is substantially vertical. The term "stirred reactor" as used herein, means a reactor having a means for agitating the reaction material in addition to the agitation caused by the flow (e.g., turbulent flow of the reaction material).

In a preferred embodiment of the present invention, the base used for the hydrolysis reaction of the $\alpha,\omega$-$C_{3\text{-}10}$alkanediol mononitrate monoacylate is aqueous NaOH, the concentration of which in water is preferably selected in the range from 1 and 50 wt.-%, more preferably from 5 and 30 wt.-%, most preferably from 7.5 and 15 wt.-%.

Advantageously, the reaction temperature for the hydrolysis reaction is selected in the range from 20 to 70° C., preferably from 30 to 60° C., most preferably from 40 to 60° C.

It is furthermore advantageous that 1 to 1.5 mol equivalents, more preferably 1.1 to 1.3 mol equivalents and most preferably 1.2 to 1.3 mol equivalents of base, preferably NaOH, based on the $\alpha,\omega$-$C_{3\text{-}10}$alkanediol mononitrate monoacylate, is used for the hydrolysis reaction.

The hydrolysis reaction is preferably carried out for a reaction time ranging from about 2 to about 6 hours, preferably from about 3 to about 5 hours, most preferably for about 4 hours.

Removal and Recovery of the Inert Solvent

In a further preferred embodiment, the process according to the present invention further comprises a step (D) (following step (C) directed to a process for removal and recovery of an inert solvent from a mixture comprising the inert solvent and an $\alpha,\omega$-$C_{3\text{-}10}$alkanediol mononitrate by distillation, said process comprising partial evaporation and condensation and continuous back-feeding of liquid fractions comprising mixtures of the inert solvent and the $\alpha,\omega$-$C_{3\text{-}10}$ alkanediol mononitrate into said distillation.

Preferably, said distillation is performed in an evaporator setup, even more preferably in an evaporated set-up comprising from 1 to 5 evaporators, more preferably 2 to 4 evaporators. An exemplary, while preferred, evaporator set-up is outlined in FIG. 4.

Said process preferably also comprises the isolation of the $\alpha,\omega$-$C_{3\text{-}10}$alkanediol mononitrate in a purity of at least 95 wt.-%, preferably at least 97 wt.-%, most preferably at least 98 wt.-%, as e.g. determined by GC chromatography using a FID detector.

Preferably, said isolated $\alpha,\omega$-$C_{3\text{-}10}$alkanediol mononitrate furthermore comprises less than 1 of the inert solvent, more preferably less than 0.5% of the inert solvent most preferably less than 0.1% of the inert solvent.

The term 'evaporator' as used herein refers to a device used to turn a liquid form of a chemical substance or a mixture of chemical substance (such as the solution of the inert solvent and the $\alpha,\omega$-$C_{3\text{-}10}$alkanediol mononitrate) into its/their gaseous-form/vapor. It is well understood, that the liquid may also be only partially evaporated, or partially vaporized, into the gas form, while part of the liquid remains liquid. Said process can be used for the separation of mixtures, e.g. by partial evaporation and partial condensation as illustrated herein.

The term condenser as used herein refers to a device or unit used to condense a gaseous substance or gaseous mixture into a liquid state through cooling.

In a particular advantageous embodiment, the solvent removal and recovery according to the present invention comprises the following steps:

(S-1) Provision of an evaporator setup comprising 3 evaporators, (S-2) Feeding of a solution comprising an $\alpha,\omega$-$C_{3\text{-}10}$alkanediol mononitrate in an inert solvent (also referred to herein as S-I) onto a first evaporator (FIG. 4: E1) and applying a pressure of 400 to 600 mbar resulting in a gaseous phase (I) (also referred to herein as GP-I) and a liquid phase (I) (also referred to herein as LP-I), wherein said liquid phase (I) comprises from about 70 to 95 wt.-% of the $\alpha,\omega$-$C_{3\text{-}10}$alkanediol mononitrate, (S-3) Feeding said gaseous phase (I) onto a first (partial) condenser (C1) to remove a first liquid fraction (also referred to herein as LF-I) by cooling to a temperature of 20 to 40° C., preferably to a temperature of 20 to 35° C., more preferably to a temperature of 25-30° C., while passing the remaining gaseous phase (II) (also referred to herein as GP-II) onto a second condenser (FIG. 4: C2), (S-4) Feeding the liquid phase (I) (LP-I) from step (S-2) onto a second evaporator (FIG. 4: E2) and applying a pressure of 50 to 150 mbar resulting in a gaseous phase (III) (also referred to herein as GP-III) and a liquid phase (II) (also referred to herein as LP-II), wherein the liquid phase (II) comprises more than 95 wt.-%, preferably more than 97 wt.-%, most preferably more than 98 wt.-% of the $\alpha,\omega$-$C_{3-10}$alkanediol mononitrate, (S-5) Feeding the gaseous phase (III) onto a third (partial) condenser (FIG. 4: C3) to remove a second liquid fraction (also referred to herein as LF-II) by cooling to a temperature of 10 to 30° C., preferably to a temperature of 20 to 30° C., more preferably to a temperature of 20 to 25° C., while passing the remaining gaseous phase (IV) (also referred to herein as GP-IV) onto a fourth condenser (FIG. 4: C4) to liquefy the inert solvent, and (S-6) Feeding the liquid phase (II) (LP-II) from step (S-4) onto a third evaporator (FIG. 4: E3) and applying a pressure of 5 to 10 mbar with the proviso that that at least one of LF-I and LF-II is fed back onto the first or the second evaporator.

It is well understood that the liquid fractions (I) and (I) still contain $\alpha,\omega$-$C_{3-10}$alkanediol mononitrate, which is recovered by said back-feeding.

An exemplary (while preferred) removal and recovery process according to the present invention is illustrated in FIG. 4.

In a partial condensation according to this invention, a vapour stream (vaporized stream) is partially condensed (liquefied) in a condenser. The remaining (not condensed) vapor is passed to a subsequent (total) condenser operated at lower temperatures to almost liquefy the remaining solvent.

Preferably, the amount of the $\alpha,\omega$-$C_{3-10}$alkanediol mononitrate in the inert solvent in step (S-2) is selected in the range from 10 to 50 wt.-%, more preferably in the range from 20 to 40 wt.-%, which is e.g. obtainable from the hydrolysis as outlined above.

The acylating agent (AA), the $\alpha,\omega$-alkanediol (AD) and water are fed into the first vessel of a vessel cascade (V1) to form the reaction mixture (ARM). The reaction mixture (ARM) is then fed onto a first distillation column (V2) and the acylating agent and water are distilled off to form a mixture (AM-I). The mixture (AM-I) is subsequently fed onto a second distillation column (V3) and the 'recycled reaction components (I)' consisting essentially of $\alpha,\omega$-alkanediol mono- and diacylate (ADMA & ADDA) are distilled off to form a mixture (AM-Ia). The mixture (AM-Ia) is then fed onto a third distillation column (V4) and ADMA is distilled off while recovering 'recycled reaction components (II)' consisting essentially of AD. During the process the recycled reaction components (I) and (II) are continuously re-fed into the first reaction vessel (V1). A small fraction (below 5%) of the recycled reaction components (I) and (II) can be purged/removed to avoid accumulation of possible formed by-products if necessary. In addition, the acylating agent as well as (part of) the water is re-fed as deemed appropriate into the first reaction vessel (V1).

Figure 1:
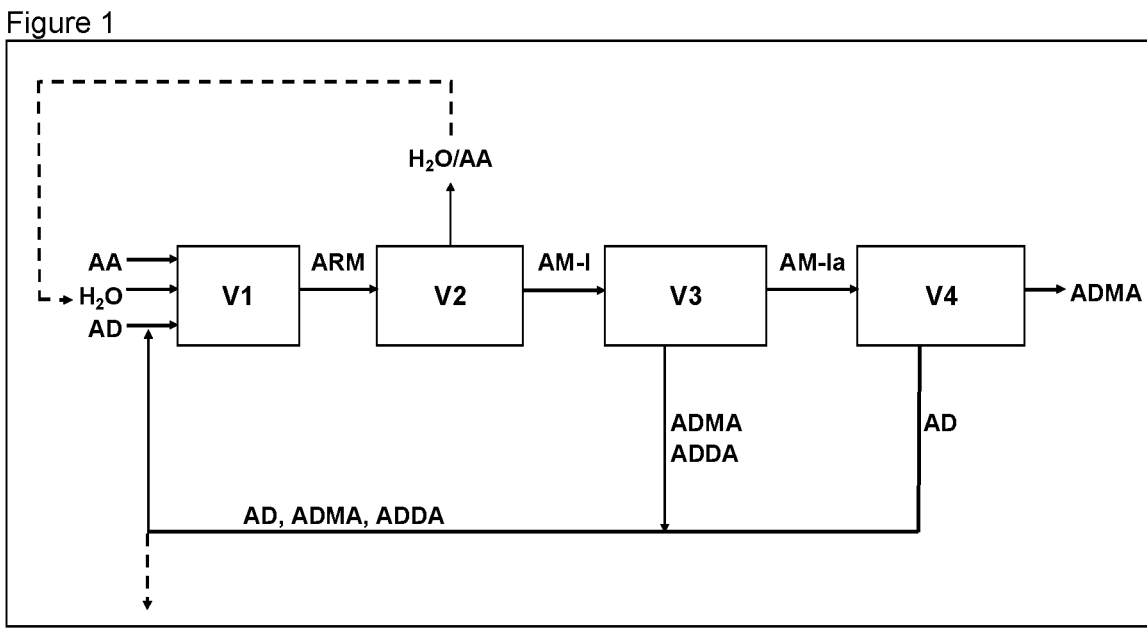
FIG. 1: In the embodiment of FIG. 1, an exemplary, but none limiting vessel cascade setup for the acylation process according to the present invention is shown.
Figure 2:
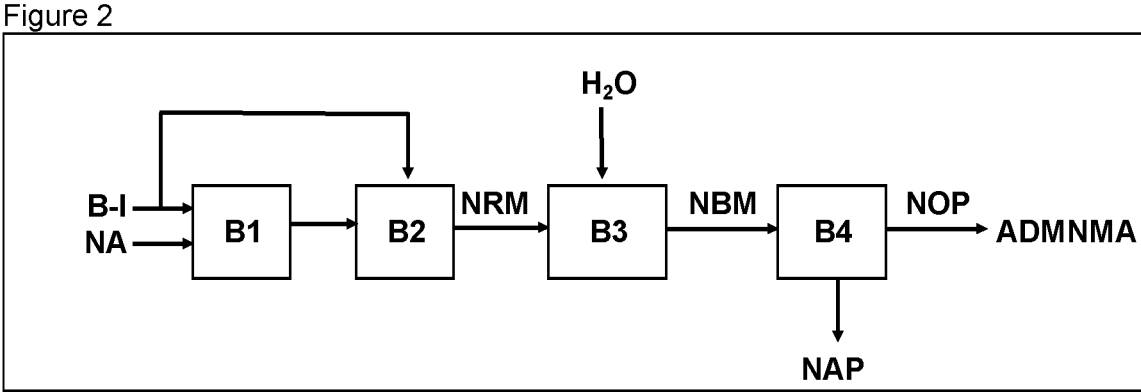

FIG. 2: In the embodiment of FIG. 2, an exemplary, but none limiting continuously operated flow-reactor setup for the nitrate ester formation according to the present invention is shown:

The nitrating agent as well as part of the solution (B-I) consisting of $\alpha,\omega$-$C_{3-10}$alkanediol monoacylate and the inert solvent are fed into a first reactor (BI), followed by adding a second portion of the solution (B-I) into the second reactor (B2). The nitrate ester formation reaction mixture (NRM) obtained after reactor (B2) is quenched in reactor B3. The thus obtained reaction biphasic mixture (NBM) is split into two phases to obtain an organic (NOP) and an aqueous phase (NAP). The $\alpha,\omega$-$C_{3-10}$alkanediol mononitrate monoacylate (ADMNMA) is in said organic phase and can be isolated thereof.

Figure 3:
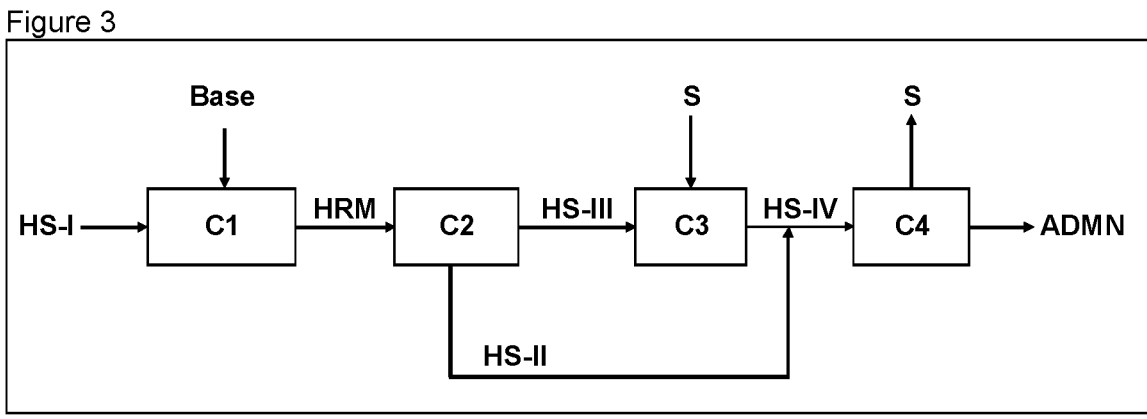

FIG. 3: In the embodiment of FIG. 3, an exemplary, but not limiting vertical, stirred cascade reactor setup for the hydrolysis process according to the present invention is shown.

The first (bottom) chamber (C1) is continuously loaded with a solution consisting essentially of an $\alpha,\omega$-$C_{3-10}$alkanediol mononitrate monoacylate and an inert solvent (HS-I) (such e.g. with the NOP obtained as outlined in FIG. 2) and an aqueous solution of a base to form a reaction mixture (HRM). The reaction mixture (HRM) is transferred into a second vessel (C2) for phase separation resulting in an organic phase (HS-II) and an aqueous phase (HS-III). The organic phase is transferred to a evaporator setup (C4) for isolation of the $\alpha,\omega$-$C_{3-10}$alkanediol mononitrate (ADMN) The aqueous phase (HS-III) is transferred into a third vessel (C3) for further extraction with the inert solvent to obtain an organic phase HS-IV) which is also transferred (combined with HS-II) to the evaporator setup (C4) to recover further ADMN.

Figure 4:
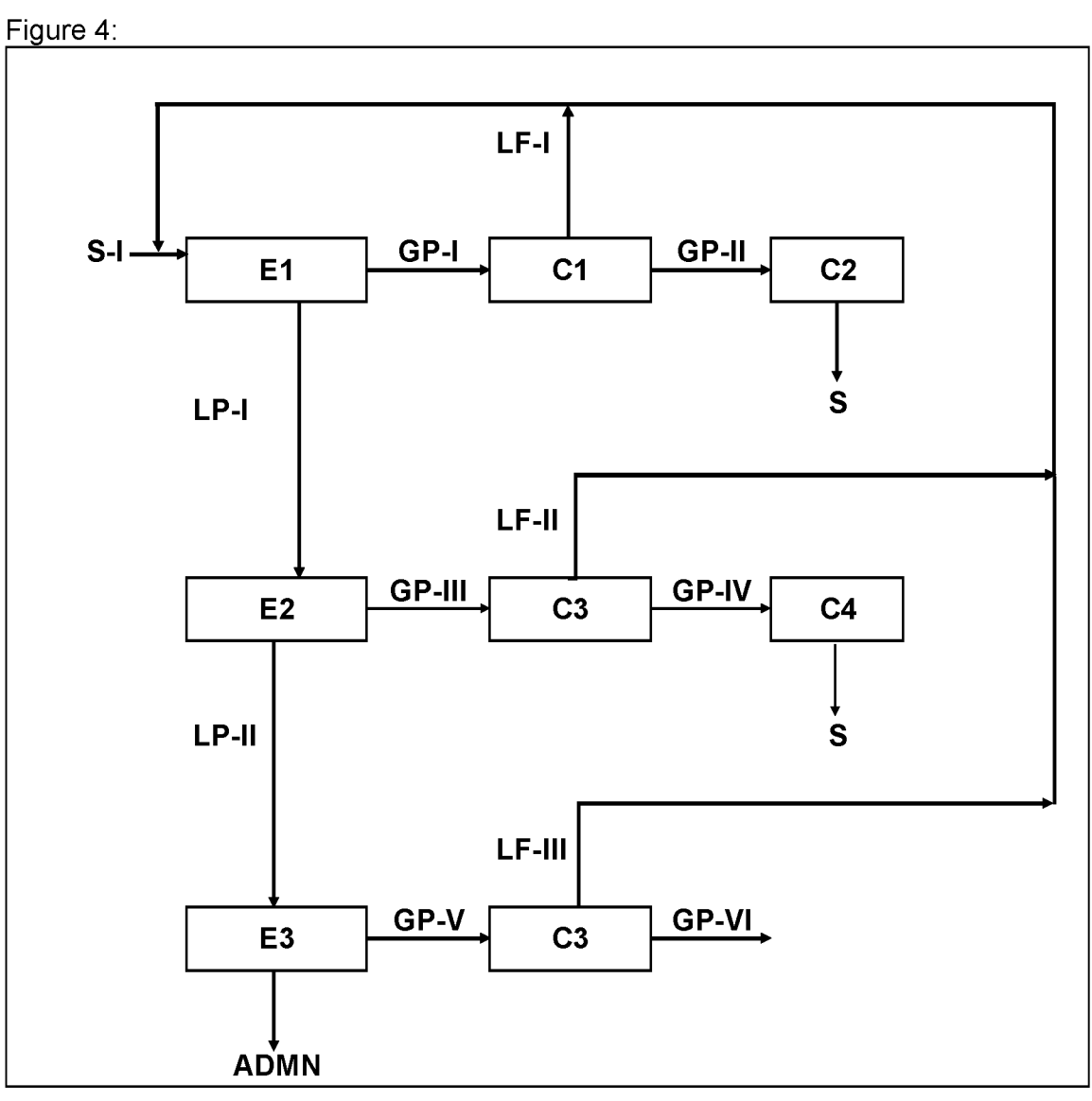

FIG. 4: In the embodiment of FIG. 4, an exemplary, but none limiting evaporator setup for the removal and recovery of the inert solvent according to the present invention is shown:

A solution comprising an $\alpha,\omega$-$C_{3-10}$alkanediol mononitrate in an inert solvent (S-I) is fed onto a first evaporator (E1) and a first liquid fraction (LF-I) is removed from the distillate of evaporator (E1) through partial condensation in a first condenser (C1) while the remaining vapors pass onto a second condenser (C2) to liquefy the remaining inert solvent (S). The liquid phase (LP-I) from evaporator (E1) is fed onto a second evaporator (E2). A second liquid fraction (LF-II) is removed from the distillate of evaporator (E2) through partial condensation in a condenser (C3), while the remaining vapors (GP-IV) pass onto a fourth condenser (C4) to liquefy the remaining inert solvent. The liquid phase (LP-II) from evaporator (E2) is fed into a third evaporator (E-3) to remove the remaining inert solvent and to recover the pure $\alpha,\omega$-$C_{3-10}$alkanediol mononitrate.

EXAMPLE

A) Acylation

The acetylation (equilibrium formation) was performed either batchwise without recycles or in a vessel cascade setup in a fully continuous process, by feeding the starting materials into a first vessel. The resulting reaction mixture from the last vessel is fed onto a first distillation column for separation (removal) of $H_2O$/HAc from PDDA/PDMA/PD. This mixture of PDDA/PDMA/PD is fed to a second rectification column for removal of PDDA from PD/PDMA. This mixture of PD/PDMA is fed to a third rectification column for separation of PDMA from PD.

Pure PDMA was obtained by rectification. Recovered PDDA, PD and HAc were recycled and fed back together with the adjusted amount of water to the reaction vessel cascade, allowing for an overall yield of 90%.

Aa) Without Using Recycling Streams (Comparative)

1,3-Propanediol (PD, 14.0 kg, 0.18 kmol, 99.7%) was mixed with Acetic Acid (HAc, 9.8 kg, 0.16 kmol, 100%). After inerting of the reactor by nitrogen flow, stirring was started (500 rpm) and the jacket temperature was increased from 20° C. to 135° C. within 70 minutes and kept at 135° C. at 4 hours and at reflux of reaction mixture. After 4 hours the jacket temperature was set to 100° C. and the pressure is slowly reduced to approx. 100 mbar abs. while removing 1.55 kg distillate. 22.0 kg residue were obtained comprising a mixture of acetic acid, water, unreacted PD (28 wt %), 3-acetylpropan-1-ol (PDMA, 44.1 wt %) and 1,3-propane-dioldiacetate (PDDA, 11.3 wt %). Yield of PDMA was 44.4% and of PDDA was 8.5% based on PD.

Removal of acetic acid/water was performed at 50 mbar abs top pressure in a rectification column DN50 with 3.5 m BX packing equipped with condenser, liquid separator for reflux adjustment and falling film evaporator with a feed rate of 6.7 kg/h and reflux ratio of 0.4-0.5 resulting in a top take off of 1.1 kg/h containing acetic acid and water and s sump stream of 5.6 kg/h (34 wt % PD, 52 wt % PDMA, 13 wt % PDDA). Removal of PDDA was performed at 20 mbar abs top pressure in a rectification column DN50 with 3.5 m BX packing equipped with condenser, liquid separator for reflux adjustment and falling film evaporator with a feed rate of 1.6 kg/h and reflux ratio of 7-8 resulting in a top take off of 0.4 kg/h containing 1 wt % PD, 40 wt % PDMA, and 54 wt % PDDA. The corresponding sump stream (1.2 kg/h) consisted of 44 wt % PD, 55 wt % PDMA, 0.3 wt % PDDA.

Separation of PDMA from PD was performed at 20 mbar abs top pressure in a rectification column DN50 with 3.5 m BX packing equipped with condenser, liquid separator for reflux adjustment and falling film evaporator with a feed rate of 1.2 kg/h and reflux ratio of 3-4 resulting in a top take off of 0.6 kg/h containing 0.5 wt % PD, 97-98 wt % PDMA, and 1 wt % PDDA. The corresponding sump stream (0.6 kg/h) consisted of 91-92 wt % PD, 8-9% PDMA. Overall Yield of PDMA during the three rectification steps was 71-73%.

Overall yield of PDMA (reaction and rectification steps) based on PD was 31-33%.

Ab) Using Recycling Streams in Fully Continuous Mode (Inventive)

1,3-Propanediol (PD, 76 kg/h, 0.99 kmol/h, 99.7%) was mixed with fresh Acetic Acid (HAc, 57 kg/h, 100%), 89 kg/h distillate from the first rectification column (56 wt % acetic acid, 44 wt % water), 90 kg/h distillate of the 2$^{nd}$ rectification column (2 wt % PD, 36.5 wt % PDMA, 61 wt % PDDA) and 110 kg/h sump stream from the third rectification column (97 wt % PD, 3% PDMA). The reaction was performed in a continuous stirred tank reactor at reflux temperature (atmospheric pressure) with a mean residence time of 5-6 hours to deliver 400 kg/h reaction mixture (mixture of acetic acid, water, unreacted PD (29 wt %), 3-acetylpropan-1-ol (PDMA, 35 wt %) and 1,3-propandiol-diacetate (PDDA, 14.5 wt %)).

Removal of acetic acid/water was performed at 50 mbar abs top pressure in a rectification column DN500 with 3.7 m BX packing equipped with condenser, liquid separator for reflux adjustment and falling film evaporator with a feed rate of 400 kg/h and reflux ratio of 0.5-1 resulting in a top take off of 85 kg/h containing acetic acid and water and sump stream of 315 kg/h (36 wt % PD, 45 wt % PDMA, 19 wt % PDDA).

Removal of PDDA was performed at 20 mbar abs top pressure in a rectification column DN1000 with 10.8 m BX packing equipped with condenser, liquid separator for reflux adjustment and falling film evaporator with a feed rate of 315 kg/h and reflux ratio of 10-15 resulting in a top take off of 92 kg/h containing 2 wt % PD, 36.5 wt % PDMA, and 61 wt % PDDA. The corresponding sump stream (223 kg/h) consisted of 50 wt % PD, 48-49 wt % PDMA, 1-2 wt % PDDA.

Separation of PDMA from PD was performed at 10 mbar abs top pressure in a rectification column DN1000 with 7.5 m BX packing equipped with condenser, liquid separator for reflux adjustment and falling film evaporator with a feed rate of 223 kg/h and reflux ratio of 5-10 resulting in a top take off of 108 kg/h containing 0.1 wt % PD, 98-99 wt % PDMA, and 1 wt % PDDA. The corresponding sump stream (115 kg/h) consisted of 98-99 wt % PD, 1-2% PDMA.

Overall yield of PDMA (reaction and rectification steps) based on (fresh) PD was 90%.

B) Nitrate Ester Formation

A 40% w/w solution of PDMA in Dichloromethane (DCM) was reacted at 5° C. in a flow-reactor with Nitro-sulfonic acid (1.1 eq HNO$_3$, 2.2 eq H$_2$SO$_4$, less than 3 wt % water).

The nitrate ester formation reaction was performed in a continuously operated flow-reactor, by mixing PDMA in DCM (60 wt % DCM/40 wt % PDMA) with Nitrosulfuric acid in a constant ratio and a steady flow of both components. To control the reaction temperature below 40° C., the reaction was partitioned by massflow between two serial flow-reactors by feeding PDMA in 2 portions (reactor 1/reactor 2=40%:60%). The overall residence time in both reactors was kept at 15-19 seconds.

Directly after the 2 sequential reactors, the reaction was diluted/quenched with water at 10° C., followed by a phase separation. The organic phase, containing the intermediate 3-acyl-propan-1-nitrate (MAMN) was washed once with water, stabilizing the mixture for intermediate storage in a buffer tank. The organic phase, containing MAMN can be subjected as-is to the next step or optionally washed with water prior to the next step , with an overall yield of 99%

The aqueous phase consisting mainly of diluted H$_2$SO$_4$ was concentrated to 65 or 96% H$_2$SO$_4$ for use in other applications.

C) Hydrolysis

PDMNMA (ca 50% in DCM) was reacted at 40-56° C. with 1,3 eq. NaOH (10-11% solution in water).

The hydrolysis of PDMNMA was performed in a vertical, stirred cascade reactor, by continuously feeding PDMNMA (ca 50% in DCM) together with 10-11% NaOH solution (in a ratio 1/1.3 eq.) from the bottom. Residence time was 4 hours, at a reaction temperature of 40-56° C. After complete conversion (>99.9%), the phases were cooled to appr. 20° C., split, and the aq. phase was washed/extracted in continuous mode with DCM (back-extraction of PDMN) at room temperature. The combined organic phases were subjected to solvent removal (see D) Workup).

The desired product is obtained in 97% yield, after removal of DCM from the combined organic phases.

D) Solvent Removal and Recovery (Partial Condensation)

After hydrolysis, the combined organic phases PDMN/DCM (77% DCM) were subjected to solvent removal in a 3-stage evaporator setup, by feeding the organic phases into a first evaporator where PDMN solution (containing 7-8% DCM) was produced at 500 mbar. The distillates (vapour stream) were directed to a partial condenser, where a liquid fraction (PDMN/DCM, ca. 55-60% PDMN) was recovered at 30° C. and fed back to the first evaporator. The remaining vapors passed to a (total) condenser operated at 0° C. to recover DCM in high purity (<0.03% PDMN).

The PDMN solution from the first evaporator (containing 7-8% DCM) is fed to a second evaporator operated at 100 mbar to produce a liquid solution containing ca. 1 wt % DCM. The distillates (vapour stream) were directed to a partial condenser, where a liquid fraction (PDMN/DCM, ca. 70-75% PDMN) was recovered at 15° C. and fed back to the first evaporator. The remaining vapors passed to a (total) condenser operated at 0° C. to recover DCM (ca. 0.1% PDMN).

The PDMN solution from the second evaporator (containing ca. 1% DCM) is fed to a third evaporator operated at 10 mbar to produce a liquid solution containing less than 0.1 wt % DCM. The distillates (vapour stream) were directed to a partial condenser, where a liquid fraction (PDMN/DCM, ca. 90% PDMN) was recovered at 0° C. and fed back to the first evaporator. The remaining vapors were discarded.

The invention claimed is:

1. A continuous process for nitrate ester formation of an $\alpha,\omega$-C$_{3-10}$alkanediol monoacylate, wherein the process comprises a step of:

reacting a nitrating agent with a solution comprising an $\alpha,\omega$-C$_{3-10}$alkanediol monoacylate and an inert solvent in a group of pieces of equipment comprising at least two reactors in series, wherein the reacting step comprises:

(i) simultaneously feeding the solution into a first reactor and a second reactor of the at least two reactors in series, and (ii) allowing the nitrating agent to react with the solution in the first and second reactors for a mean residence time of about 5 seconds to about 30 seconds.

2. The process for the continuous nitrate ester formation according to claim 1, wherein step (i) comprises feeding 40 to 60% of the total mass flow of the solution into the first reactor, while simultaneously feeding a remaining portion of the total mass flow of the solution into the second reactor.

3. The process for the continuous nitrate ester formation according to claim 1, wherein the $\alpha,\omega$-C$_{3-10}$alkanediol monoacylate in the inert solvent in a concentration of from 10 to 60 wt.-%.

4. The process for the continuous nitrate ester formation according to claim 1, wherein the nitrating agent is a mixture of H$_2$SO$_4$ and HNO$_3$, wherein a) the mol ratio of HNO$_3$ to the $\alpha,\omega$-C$_{3-10}$alkanediol monoacylate is selected in the range from 1 to 1.5, and b) the mole ratio of the H$_2$SO$_4$ to the HNO$_3$ is selected in the range from 1.5 to 2.5.

5. The process for the continuous nitrate ester formation according to claim 1, wherein the reaction volume ratio of the first reactor to the second reactor is selected in the range from 4:1 to 1:4.

6. The process for the continuous nitrate ester formation according to claim 1, wherein the mean residence time of the solution in the first and second reactors is about 10 to about 20 seconds.

7. The process for the continuous nitrate ester formation according to claim 1, wherein a) the first reactor has an outlet reaction temperature which is equal to or below 40° C., and b) the second reactor has an outlet reaction temperature which is equal to or below 25° C.

8. The process for the continuous nitrate ester formation according to claim 1, wherein the process forms an $\alpha,\omega$-C$_{3-10}$ alkanediol mononitrate, and wherein the process further comprises a step (A) preceding the reacting step which consists of:

(A) an acylation reaction step by conducting an acylation reaction of an $\alpha,\omega$-C$_{3-10}$alkanediol with an acylation agent, wherein $\alpha,\omega$-C$_{3-10}$alkanediol monoacylate and $\alpha,\omega$-C$_{3-10}$alkanediol diacylate back into the acylation reaction such that the acylation reaction comprises adding water in an amount of 0.5 to 1.5 mole per mole of recycled acylate groups, and a molar ratio of a molar sum of the acylating agent, $\alpha,\omega$-C$_{3-10}$alkanediol monoacylate and 2 times of $\alpha,\omega$-C$_{3-10}$alkanediol diacylate to the sum of the $\alpha,\omega$-C$_{3-10}$alkanediol, $\alpha,\omega$-C3-10alkanediol monoacylate and $\alpha,\omega$-C$_{3-10}$alkanediol diacylate is in a range from 0.5 to 1.1 mol per mol of $\alpha,\omega$-C3-10alkanediol, and wherein the process comprises a step (C) and optionally a step (D) subsequent to the reacting step which consist of:

(C) conducting a two-phase hydrolysis of the $\alpha,\omega$-C3-10alkanediol mononitrate monoacylate by continuously feeding a base and a solution comprising the $\alpha,\omega$-C3-10alkanediol mononitrate monoacylate and an inert solvent into a cascade reactor to obtain a solution comprising the inert solvent and $\alpha,\omega$-C3-10alkanediol mononitrate, and optionally (D) removing and recovering the inert solvent from the solution by distillation, the process comprising partial condensation and continuous back-feeding of liquid fractions comprising mixtures of the inert solvent and $\alpha,\omega$-C3-10alkanediol mononitrate into the distillation.

9. The process according to claim 8, wherein the acylation reaction step (A) is a continuous process carried out in a vessel cascade set-up.

10. The process according to claim 8, wherein the acylation reaction step (A) comprises a separation step comprising separating the $\alpha,\omega$-C$_{3-10}$alkanediol monoacylate such that:

a) an amount of $\alpha,\omega$-C$_{3-10}$alkanediol in the $\alpha,\omega$-C$_{3-10}$alkanediol monoacylate is less than 0.5 wt.-%, and/or b) an amount of the $\alpha,\omega$-C$_{3-10}$alkanediol diacylate in the $\alpha,\omega$-C$_{3-10}$alkanediol monoacylate is less than 5 wt. %.

11. The process according to claim 8, wherein the acylation agent in the acylation reaction step (A) is a carboxylic acid.

12. The process according to claim 8, wherein the two-phase hydrolysis step (C) comprises continuously feeding the base and the solution comprising an $\alpha,\omega$-C$_{3-10}$alkanediol mononitrate monoacylate and an inert solvent a stirred cascade reactor.

13. The process according to claim 8, wherein the base in the two-phase hydrolysis step (C) is selected from the group consisting of NaOH, KOH, Ca(OH)$_2$, ammonia, and aqueous solutions thereof.

14. The process according to claim 8, wherein the two-phase hydrolysis step (C) comprises continuously feeding an aqueous solution of the base in a concentration of from 1 to 50 wt.-%.

15. The process according to claim 8, wherein the two-phase hydrolysis step (C) is conducted at a reaction temperature of 20 to 70° C.

* * * * *